US005840581A

United States Patent [19]
Carraway et al.

[11] Patent Number: 5,840,581
[45] Date of Patent: Nov. 24, 1998

[54] PROCESS FOR SOMATIC EMBRYOGENESIS OF SWEETGUM

[75] Inventors: Daniel T. Carraway, Bainbridge; Scott A. Merkle, Athens, both of Ga.

[73] Assignee: International Paper Company, Purchase, N.Y.

[21] Appl. No.: 626,235

[22] Filed: Mar. 29, 1996

[51] Int. Cl.$^6$ .............................. C12N 5/00; C12N 5/02
[52] U.S. Cl. .................. 435/430.1; 435/420; 435/422; 435/431
[58] Field of Search .................. 435/430.1, 420, 435/422, 431

[56] References Cited

U.S. PATENT DOCUMENTS

| 4,801,545 | 1/1989 | Stuart et al. | 435/240.45 |
|---|---|---|---|
| 4,818,693 | 4/1989 | Stuart et al. | 435/240.49 |
| 4,957,866 | 9/1990 | Gupta et al. | 435/240.4 |
| 5,187,092 | 2/1993 | Uddin | 435/240.45 |
| 5,304,725 | 4/1994 | Nelson | 800/200 |
| 5,413,930 | 5/1995 | Becwar et al. | 435/430.1 |

OTHER PUBLICATIONS

Witham F.H., Blaydes D.F., Devin R.M. 1971. Experiments in Plant Physiology. VanNostrand–Reinhold Company. NY. Table 51–1.
Lopez–Baez O, Bollon H, Eskes A, Petiard V. 1993. Somatic Embryogenesis and Plant Regeneration From Flower Parts of *Theobroma cacao* L. C.R. Acad. Sci. Paris/Life Sciences. 316:579–584.
F. Carimi, F.D. Pasquela, F.G. Crescimanno. 1994. Somatic Embryogenesis From Styles of Lemon (citrus limon). Plant Cell Tissue Organ Cult. 37:209–211.
Gingas VM. 1991. Asexual Embryogenesis and Plant Regeneration From Male Catkins of Quercus. HortScience 26:1217–1218.
Gupta PK, Timmis R, Mascarenhas AF. 1991. Field Performance of Micropropagated Forestry Species. In Vitro Cell. Dev. Biol. 27P:159–164.
Jorgensen J. 1989. Somatic Embryogenesis in *Aesculus hippocastaneum*L. By Culture of Filament Callus. J. Plant Physiol. 135:240–241.
Jorgensen J. 1991. Androgenesis in *Quercus petraea, Fagus sylvatica* and *Aesculus hippocastanum*. In Woody Plant Biotechnology (M.R. Ahuja, ed.). Plenum Press, New York. pp. 353–354.
Kim SW, Song NH, Jung KH, Kwak, SS, Liu JR. 1994. High Frequency Plant Regeneration From Anther –Derived Cell Suspension Cultures Via Somatic Embryogenesis in *Catharatithus roseus*. Plant Cell Rep. 13:319–322.
Lloyd G, McCown B. 1980. Commerically–feasible Micropropagation of Mountain Laurel, *Kalmia latifolia*, by Use of Shoot–tip Culture. Proc. Int. Plant Propag. Soc. 30:421–427.
Lu, C.Y. 1993. The Use of Thidrazuron in Tissue Culture. In Vivo Cell. Dev. Biol. 29 pp. 92–96.
Michler CH, Bauer EO. 1991. High Frequency Somatic Embryogenesis From Leaf Tissue Populus Spp. Plant Sci. 77:111–118.

(List continued on next page.)

*Primary Examiner*—Ponnathapura Achutamurthy
*Assistant Examiner*—Hankyel T. Park
*Attorney, Agent, or Firm*—Luedeka, Neely & Graham P.C.

[57] ABSTRACT

The present invention relates to an improved method for generating somatic embryos from mature plant tissue. The treatment methods of the present invention use a combination of disinfestation procedures and plant growth regulator compositions which induce unequal cell division. After forming and maturing the somatic embryos on suitable growth media, the mature somatic embryos are desiccated and cold stratified resulting in an dramatic increase in the percentage of somatic embryos which may be converted into plants.

30 Claims, 5 Drawing Sheets

OTHER PUBLICATIONS

Murashige T, Skoog F. 1962. A Revised Medium For Rapid Growth and Bioassays With Tobacco Tissue Cultures. Physiol. Plant. 15:473–497.

Park, Y.G., and S.H. Son. 1988. In Vitro Organogenesis and Somatic Embryogenesis From Punctured Leaf of *Populus nigra* x *P. maximowiczii*. Plant CellOrgan Cult. 15:95–105.

Sharp WR, Sondahl MR, Caldas LS, Maraffa SB. 1980. The Physiology of In Vitro Asexual Embryogenesis. In Horticultural Reviews, vol. 2,(J.Janick, ed.). AVI Publishing Co., Westport, CT. pp. 268–310.

Somer HE, Brown CL. 1980. Embryogenesis in Tissue Cultures of Sweetgum. Forest Sci. 26:257–260.

Wang, Lo, Boa, X–M, Liu, YH, Hao, S. 1994. Origin of Direct Somatic Embryos From Cultures Inflorescence Axis Segments of *Freesia refracta*. Int. J. Plant Sci. 155(6):672–676.

PROCESS FOR SOMATIC EMBRYOGENESIS OF SWEETGUM

FIELD OF THE INVENTION

This invention relates to methods for selective propagation of sweetgum and in particular to propagation of sweetgum by somatic embryogenesis.

BACKGROUND

The sweetgum (*Liquidambar styraciflua* L.) is a commercially important species particularly for the pulp and paper industry. Unfortunately, current methods for propagation of sweetgum do not provide for clonal production of plants of a proven genetic value on a scale that would be commercially viable.

Since many factors can influence the characteristics of a tree throughout its life, it is desirable to propagate only trees having a proven genotype and which can flourish in a particular region, rather than propagating trees from immature explant material for which the characteristics are as yet unknown. While many methods exist for generating trees which may be successful in a region, no method is known which is capable of producing a high number of trees from a selected individual mature tree. "Mature" means a substantially fully grown tree and not a seedling.

In the field of plant propagation, U.S. Pat. No. 4,818,693 to Stuart et al. describes methods and compositions for generating somatic embryos from immature plant somatic tissue. Stuart et al. start with somatic tissue obtained from the seeds of various plants. While Stuart et al. have been successful in stimulating embryogenesis from immature plant tissue, the methods of Stuart et al. have not succeeded in producing somatic embryos from mature plant tissue. Accordingly, plants generated by the methods of Stuart et al. will not necessarily have the particular genetic code which make the plants successful in a particular environment.

Embryogenesis of tissue cultures from the hypocotyl of sweetgum seedlings was reported in "Embryogenesis in Tissue Cultures of Sweetgum," by H. E. Sommer and C. L. Brown, *Forest Science*, 26, No. 2, June 1980, pp. 257–260. However, it was found that the yield of embryos was low. Furthermore, since the tissue is obtained from the hypocotyl of the seedlings rather than from mature tissue of plants, the seedlings generated from the tissue do not necessarily have a desirable genotype.

Jörg Jörgensen describes a method for somatic embryogenesis in a paper entitled "Somatic embryogenesis in *Aesculus hippocastanum* L. by Culture of Filament Callus," *Journal of Plant Physiology*, 135, 1989, pp. 240–241. In his paper, Jörgensen describes the development of adventitious embryos from filaments of the flowers of 10–100 year old trees. However, the methods described by Jörgensen have been found to be unsuitable for mass production of proembryogenic masses and not suitable for producing somatic embryos of sweetgum.

In a paper entitled "High Frequency Somatic Embryogenesis From Leaf Tissue of Populus ssp.," by Charles H. Michler and Edmund O. Bauer, *Plant Science*, 77, 1991, pp. 111–118, the authors describe their efforts to produce somatic embryos from a hybrid poplar. According to Michler and Bauer, the somatic embryos which were obtained from a cell suspension culture had an array of aberrant structures in association with embryos with normal morphology. The abnormal morphology included fused cotyledons, fused embryos, shortened hypocotyls and multiple cotyledons and radicles. Based on their results, Michler and Bauer concluded that if embryogenic callus is properly selected, highly morphogenic cultures may be maintained for long periods of time and mature somatic embryos may be obtained. However, the methods of Michler and Bauer are experimental and require additional studies to determine how to control abnormal embryo morphology and developmental synchrony.

The above and other known prior efforts to provide a commercially viable propagation method for somatic embryos from mature plant tissue have been largely unsuccessful. These failures have become a limiting factor in the advancement of the tree cultivation industry and in the art of plant cultivation in general.

It is therefore an object of the invention to provide a method for propagation of woody plant species of a known phenotype.

Another object of the invention is to provide a commercially viable method for propagation of sweetgum from a mature tree with known genetic characteristics.

Yet another object of the invention is to provide a method for cloning plants which can be used to propagate large numbers of individual plants from genetically successful mature plant tissue.

Still another object of the invention is to improve the yield of embryos obtained from mature plant tissue.

Another object of the invention is to increase the yield of somatic embryos from tissue collected from mature sweetgum which may be successfully converted into trees.

SUMMARY OF THE INVENTION

With regard to the foregoing and other objects, the present invention provides a method for producing embryos for propagation of sweetgum. The method comprises collecting inflorescence tissue, preferably male inflorescence tissue, from a mature sweetgum tree. The tissue is first disinfested to substantially eliminate fungal and bacterial propagules from the tissue. Once the tissue is disinfested, selected portions of the tissue are cultured using a cell growth medium containing from about 0.01 to about 2.5 milligrams per liter of N-phenyl-N-1,2,3-thiadiazol-5-ylurea (TDZ).

The present invention provides a method for propagating large numbers of economically important trees on a scale that is suitable for commercialization. An important advantage of the embryogenic methods of the invention over methods which rely on the production of adventitious buds or multiplication of axillary buds from tree cuttings is the potential for very high frequency regeneration of the plants. Virtually unlimited numbers of embryos can be generated from a single explant. In addition, the proembryogenic cultures can be grown in liquid which allows production and handling of thousands of proembryonic masses at one time. Furthermore, the tissue used to propagate the trees may be obtained from mature trees of known genetic value (known phenotype) thereby reducing the risk that the propagated trees will not survive or will not thrive in the environment where they are to be grown. While the present methods are directed particularly to the propagation of sweetgum, it is believed that the methods may be adapted for use in propagating other woody species.

BRIEF DESCRIPTION OF THE DRAWINGS

The above and other features and advantages of the invention will be further described in the following detailed description in conjunction with the drawings in which.

DETAILED DESCRIPTION OF THE INVENTION

Figure 1:
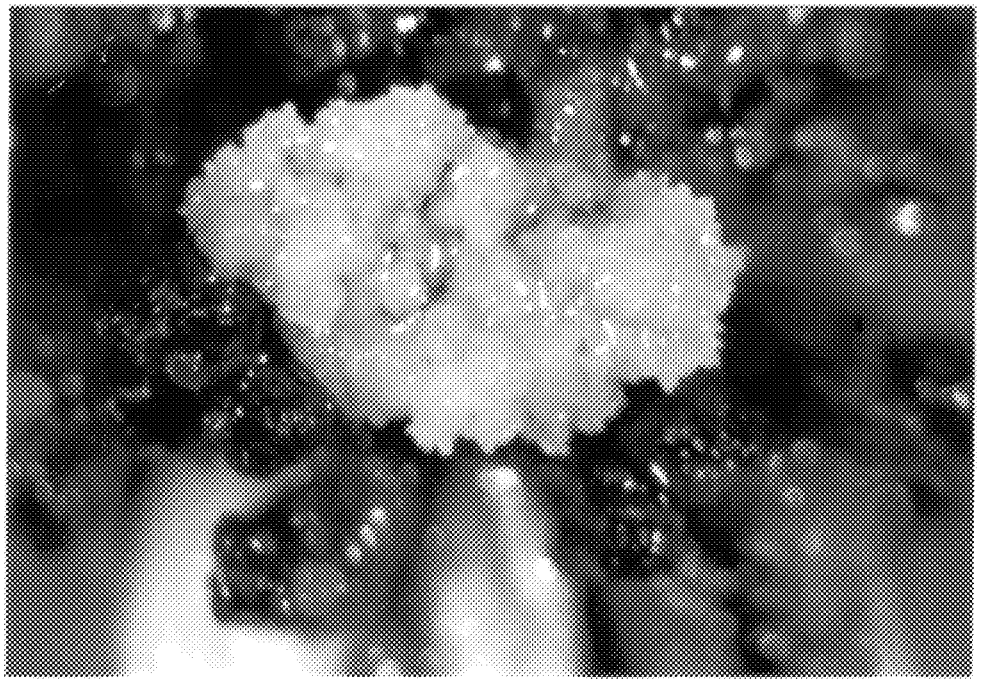
FIG. 1 is a photomicrograph of proembryogenic masses arising from an anther cluster.

In order to propagate sweetgum according to the methods of the invention, it is preferred to collect male inflorescence tissue from one or more designated sweetgum. It is particularly preferred to collect expanding buds containing staminate inflorescences from the source trees. While the least expanded inflorescences may give the highest embryogenic response, buds at any developmental stage from the beginning of bud expansion up to pollen release may be used. The collected inflorescences from the donor tree preferably have an average length of about 12 mm, which is typically about 35% of the length of the most elongated buds.

After collection of the buds, the bracts are removed and the buds are surface disinfested by methods which substantially eliminate fungal and bacterial propagules from the inflorescence tissue. Initially, the buds are hand washed in cool water using a liquid dish detergent. After washing the buds in water containing detergent, the buds are further disinfested by use of a combination of washing steps under essentially sterile conditions. The washing steps include the use of about 70% (vol./vol.) ethanol for about 30 seconds to about 5 minutes, about 30% (vol./vol.) disinfectant wash solution for about 2 to about 15 minutes, about 10 to about 30% (vol./vol.) sodium hypochlorite solution containing about 5% (vol./vol.) sodium hypochlorite for about 2 to about 15 minutes and sterile water for about 2 to about 30 minutes. It is particularly preferred to include a wash step with 3% (vol./vol.) hydrogen peroxide prior to a final sterile water wash. One or more of the wash steps may include the use of a surfactant to enhance the action of the wash solutions on the bud surfaces. During the washing procedure, outer bud scales from the buds are removed under a microscope, preferably under sterile conditions.

After disinfesting the buds, the clumps of stamens are detached from the axes and the clumps are sliced, preferably in half. While it is preferred to culture cells from the stamens, the axes may also be sliced and cultured in accordance with the procedure of the invention.

The inflorescence parts are cultured on a first plant growth medium. The first plant growth medium is a basal medium of solidified agar containing TDZ and, optionally, 2,4-dichlorophenoxyacetic acid (2,4-D). A preferred basal medium may be selected from a Woody Plant medium (WPM) which is described in "Commercially-feasible micropropagation of mountain laurel, *Kalmia latifolia*, by use of shoot-tip culture," *Proc. Int. Plant Propag. Soc.*, 30, 1980, pp. 421–427 or a modified Blaydes medium as described in *Experiments in Plant Physiology*, by F. H. Witham, D. F. Blaydes and R. M. Devlin, Van Nostrand-Reinhold, New York, 1971, 245 pages. Other commercial basal media may also be used in combination with TDZ and, optional, 2,4-D.

The amount of TDZ used in the medium preferably ranges from about 0.01 to about 5 milligrams per liter, most preferably from about 0.01 to about 2.5 milligrams per liter and the amount of 2,4-D in the medium preferably ranges from about 0.01 to about 3 milligrams per liter, most preferably from about 0.01 to about 1.5 milligrams per liter.

The inflorescence parts may be continuously cultured on a single plant growth medium containing TDZ and, optionally, 2,4-D. The parts may also be pulsed during the culturing period by maintaining the parts on basal medium for 1 to 30 days and on a medium containing TDZ for 1 to 30 days over a total period of time of about 6 months.

Within about 6 months, somatic embryos and proembryogenic masses (PEMs) usually appear on the first medium. PEMs are the undifferentiated, densely cytoplasmic cells which arise subsequent to unequal cell division in explant tissue and which have the potential to form somatic embryos. FIG. 1 illustrates the appearance of typical PEMs on an anther cluster magnified about 10 times.

Figure 2:
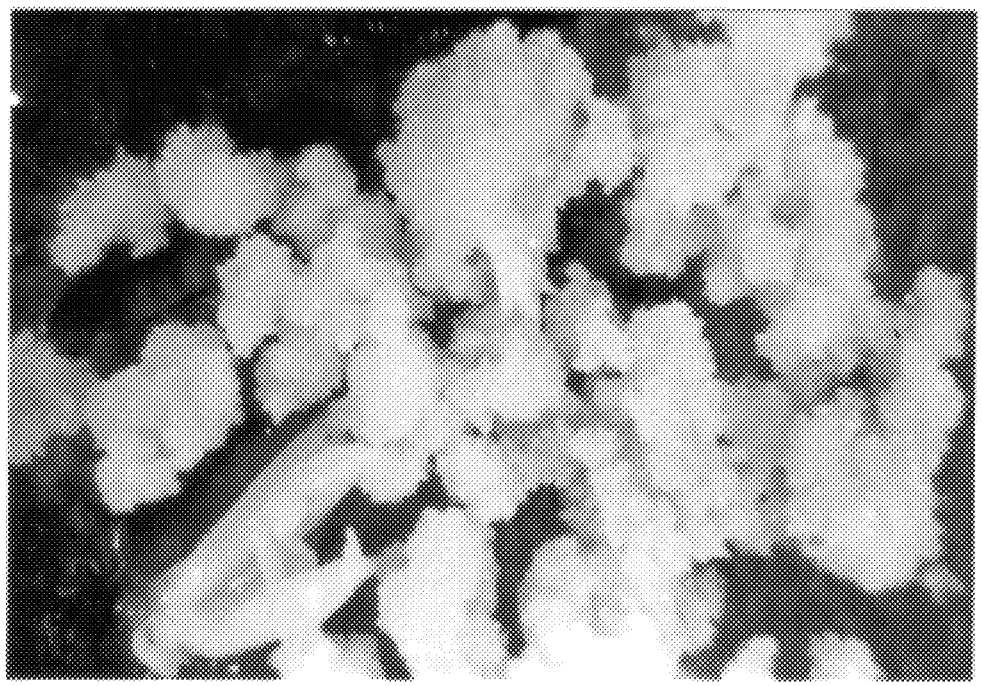
FIG. 2 is a photomicrograph of proembryogenic masses which have been multiplied according to the methods of this invention.

The somatic embryos are transferred to a second growth medium which is comparable to the first medium for additional growth before maturation treatment. Visual inspection of the first medium is used to select the PEMs having the greatest potential for developing into additional somatic embryos. Preferred PEMs have relatively small vacuoles and dense cytoplasm. Cells with relatively large vacuoles are not particularly suitable for the embryogenesis methods of this invention. The selected PEMs are transferred to a liquid medium, preferably on a rotary shaker, where they are cultured in order to increase the total mass of PEMs. FIG. 2 illustrates the appearance of the PEMs after multiplication treatment, magnified about 10 times. The liquid medium for multiplying the PEMs has a composition similar to the first plant growth medium.

After culturing the PEMs for about two months, the PEMs are size fractionated preferably through a stainless steel mesh screen having apertures with a size ranging from about 100 to about 400 microns. After fractionating the PEMs, the PEMs are collected on sterile filter paper and plated onto a growth medium containing activated charcoal and substantially no growth regulators. The concentration of activated charcoal on the growth medium ranges from about 0.25 to about 20 grams per liter and is sufficient to absorb substantially all of the TDZ or 2,4-D which may be in the PEMs which are collected on the filter paper.

Figure 3:
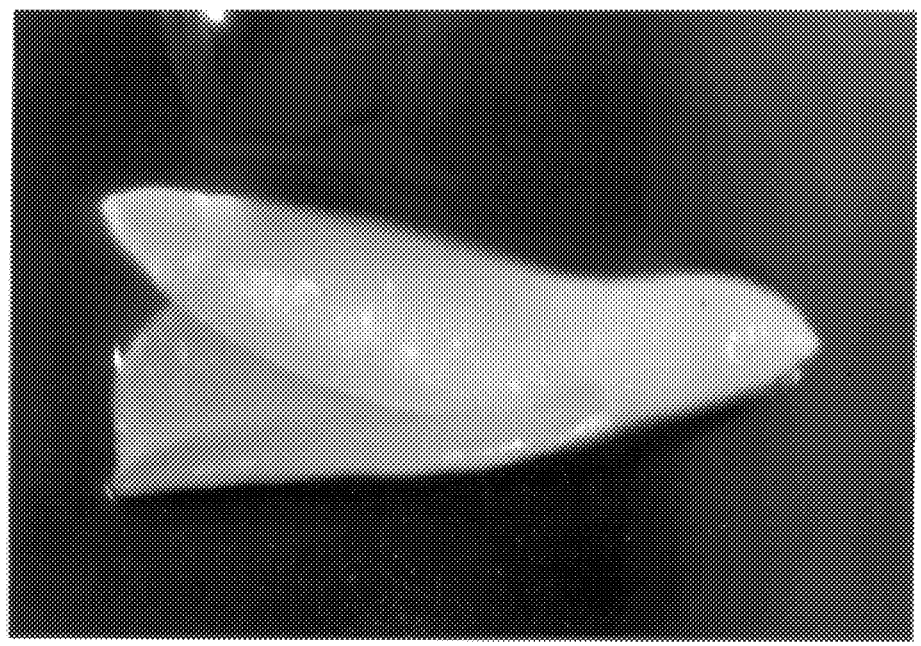
FIG. 3 is a photomicrograph of a mature somatic embyro obtained from the proembryogenic mass.

Both the somatic embryos which initially formed on the first medium and the somatic embryos which formed from the PEMs on charcoal containing growth medium are subjected to maturation treatment. The maturation treatment includes the use of abscisic acid (ABA), and, optionally, one or more sugars. The abscisic acid is used to inhibit the embryos so that they do not undergo precocious germination. The amount of ABA in the medium is preferably in an amount ranging from about 0.5 to about 3 milligrams per liter. The optional sugars which may be used with the ABA may be selected from glucose, fructose, maltose, sucrose and the like. Particularly preferred sugars are maltose and sucrose. The amount of sugar used with the maturation medium may range from about 20 to about 100 grams per liter of each, most preferably from about 30 to about 90 grams per liter. The entire maturation treatment period typically ranges from about 1 to about 8 weeks or until the somatic embryos have accumulated sufficient energy reserves for later development of the plant. FIG. 3 is an illustration of a mature somatic embryo obtained by the process of this invention (magnified about 20 times). In the photomicrograph, the embryo shown is about 5 millimeters long.

After maturation is substantially complete, the somatic embryos are desiccated under conditions sufficient to reduce the moisture content of the embryos to from about 8 to about 75 percent by weight of the moisture content of the embryos at the end of the maturation period. Desiccating the embryos has been found to be useful for increasing the number of embryos which eventually germinate.

Figure 4:
FIG. 4 is a photograph of a sweetgum grown from a somatic embryo of the invention.

The desiccated embryos are then cold stratified for from about 2 to about 8 weeks at a temperature ranging from about 1° to about 10° C. Cold stratification enhances the somatic embryos' ability to grow shoots. It has been found that by combining desiccation with cold stratification, 90 percent or more of the somatic embryos may be converted to plants. Use of cold stratification alone or desiccation alone results in the formation of plants from only about 30 to about 50 percent of the somatic embryos. A sweetgum derived from a somatic embryo obtained by using the process of this invention is shown in FIG. 4.

An important feature of the invention is the discovery of improved disinfection procedures and cell growth methods which may be used for inducing unequal cell division from mature explant tissue. While not desiring to be bound by theoretical considerations, it is believed that the disinfection procedures using hydrogen peroxide in one of the wash steps in combination with the use of TDZ in a growth medium to induce unequal cell division, significantly increase the yield of embryogenic cells obtained from mature explant tissue. While TDZ is preferred, other cytokinin-like compounds may be used provided they induce unequal cell division in the explant tissue.

In the following example, various features of the invention are illustrated. The examples are not intended to limit the invention in any way.

EXAMPLE

For purposes of disinfesting explant tissue, the buds were first washed in a beaker containing cool water (25° C.) and 3 drops of a liquid dish washing detergent (DAWN detergent). After washing the buds, sterile glassware under a sterile hood was used for the remaining disinfestation steps. The buds were washed as follows for the time indicated:

| Wash Composition | Wash time in minutes |
|---|---|
| 70% (vol./vol.) ethanol | 1 |
| 30% (vol./vol.) BROAD-CIDE 128 disinfectant (available from Osceola Supply, Inc. of Tallahassee, FL) | 5 |
| 30% (vol./vol.) CLOROX bleach | 5 |
| sterile water | 2 |
| sterile water | 5 |

After the initial wash, the outer bud scales were removed inside of a laminar flow hood under a microscope which had been sterilized with 70% (vol./vol.) isopropyl alcohol. The buds were then washed in accordance with the following procedure:

| Wash Composition | Wash time in minutes |
|---|---|
| 70% (vol./vol.) ethanol | 3 |
| 30% (vol./vol.) BROAD-CIDE 128 disinfectant | 5 |
| 10% (vol./vol.) CLOROX bleach | 5 |
| sterile water | 2 |
| sterile water | 10 |

The remaining bud scales were removed under a sterile hood and with a sterilized microscope and the buds were washed using the following procedure:

| Wash Composition | Wash time in minutes |
|---|---|
| 3% (vol./vol.) hydrogen peroxide containing 5 drops of TWEEN 20 per 100 milliliters (TWEEN 20 is a wetting agent available from Fisher Scientific of Fairlawn, NJ) | 10 |
| sterile water | 2 |

The compositions of various growth media used for inducing unequal cell division are contained in the following table:

TABLE 1

| Sample # | Component 1 | Amount mg/L | Component 2 | Amount mg/L |
|---|---|---|---|---|
| 1 | TDZ[1] | 0.01 | — | — |
| 2 | TDZ | 0.05 | — | — |
| 3 | TDZ | 0.10 | — | — |
| 4 | TDZ | 0.50 | — | — |
| 5 | TDZ | 1.00 | — | — |
| 6 | TDZ | 0.01 | 2,4-D[2] | 0.01 |
| 7 | TDZ | 0.01 | 2,4-D | 0.05 |
| 8 | TDZ | 0.05 | 2,4-D | 0.01 |
| 9 | TDZ | 0.05 | 2,4-D | 0.05 |
| 10 | TDZ | 0.10 | 2,4-D | 0.01 |
| 11 | TDZ | 0.10 | 2,4-D | 0.05 |
| 12 | TDZ | 0.50 | 2,4-D | 0.01 |
| 13 | TDZ | 0.50 | 2,4-D | 0.05 |
| 14 | TDZ | 1.00 | 2,4-D | 0.01 |
| 15 | TDZ | 1.00 | 2,4-D | 0.05 |
| 16 | TDZ | 0.01 | NAA[3] | 0.50 |
| 17 | TDZ | 0.01 | NAA | 1.00 |
| 18 | TDZ | 0.05 | NAA | 0.50 |
| 19 | TDZ | 0.05 | NAA | 1.00 |
| 20 | TDZ | 0.10 | NAA | 0.50 |
| 21 | TDZ | 0.10 | NAA | 1.00 |
| 22 | TDZ | 0.50 | NAA | 0.50 |
| 23 | TDZ | 0.50 | NAA | 1.00 |
| 24 | TDZ | 1.00 | NAA | 0.50 |
| 25 | TDZ | 1.00 | NAA | 1.00 |
| 26 | — | — | — | — |
| 27 | TDZ | 1.00 | 2,4-D | 0.50 |
| 28 | TDZ | 1.00 | 2,4-D | 0.10 |
| 29 | TDZ | 0.50 | 2,4-D | 0.50 |
| 30 | TDZ | 0.50 | 2,4-D | 0.10 |
| 31 | TDZ | 0.05 | 2,4-D | 0.025 |
| 32 | BA[4] | 0.25 | 2,4-D | 1.00 |
| 33 | TDZ | 0.05 | 2,4-D | 0.10 |
| 34 | TDZ | 0.10 | 2,4-D | 0.10 |
| 35 | TDZ | 0.05 | 2,4-D | 0.50 |
| 36 | TDZ | 0.10 | 2,4-D | 0.50 |

Figure 5:
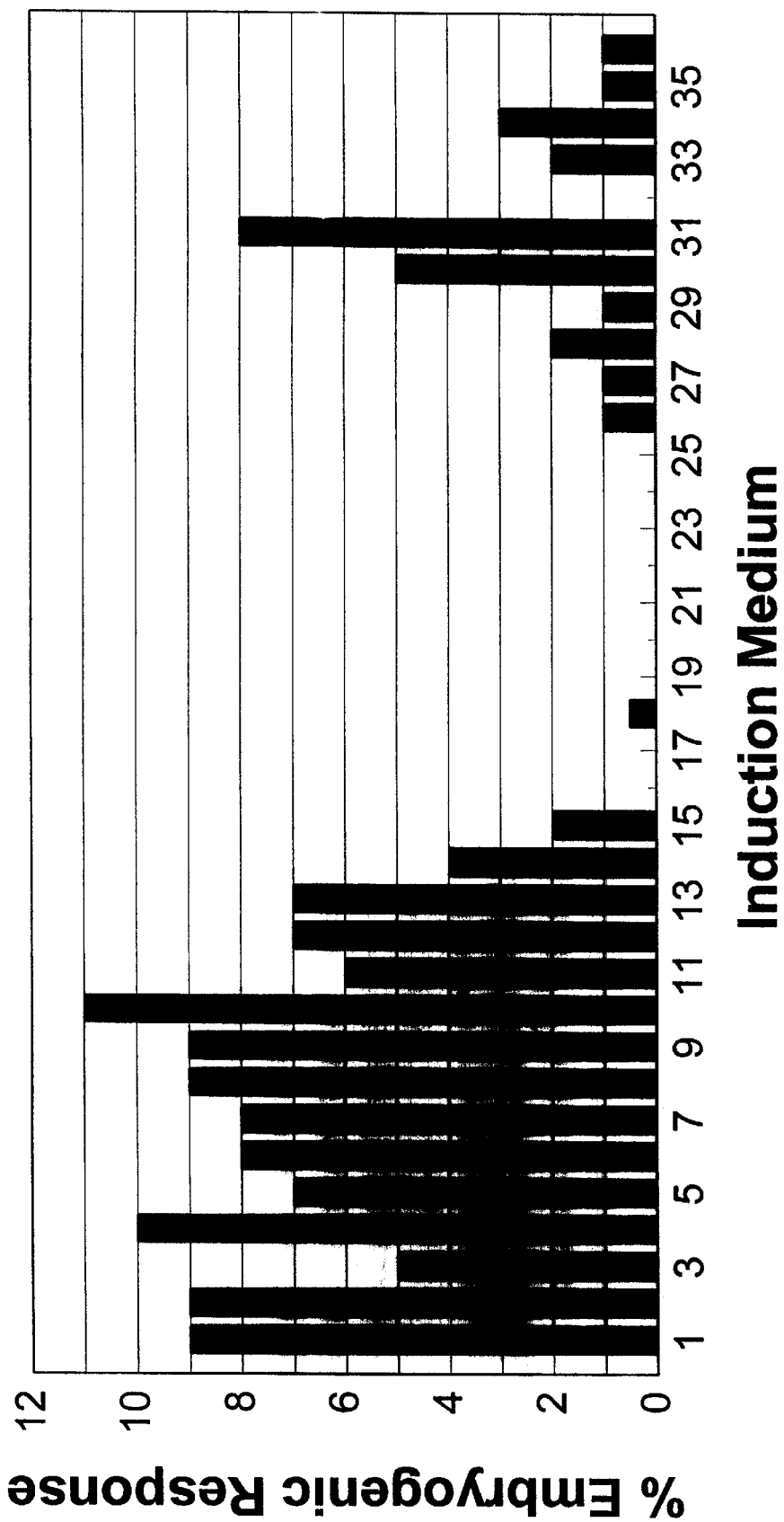
FIG. 5 is a graphical illustration of the embryogenic response for various embryo induction media.

[1]TDZ - N-phenyl-N-1,2,3-thiadiazol-5-ylurea
[2]2,4-D - 2,4-dichlorophenoxyacetic acid
[3]NAA - naphthalene acetic acid
[4]BA - 6-benzlyadenine Of the foregoing samples, a successful media was determined by which media induced any growth whatsoever of somatic embryos from the plant tissue. Of the foregoing, media numbers 1–15, 26–31 and 33–36 were successful for inducing the production of somatic embryos. Media containing TDZ in combination with NAA (Samples 17–25) appeared to be less successful for inducing growth of somatic embryos. The results of the induction of somatic embryos on the media containing the components listed in Table 1 are graphically illustrated in FIG. 5.

In the following table, the compositions of the maturation media which were used are shown.

TABLE 2

| Sample | ABA | | Polyethylene Glycol | | Maltose | | Sucrose | |
|---|---|---|---|---|---|---|---|---|
| Media # | mg/L | μg/125 mL | g/L | g/125 mL | g/L | g/125 mL | g/L | g/125 mL |
| 1 | — | — | — | — | 30 | 3.75 | — | — |
| 2 | — | — | — | — | 60 | 7.5 | — | — |
| 3 | — | — | — | — | 90 | 11.25 | — | — |
| 4 | — | — | — | — | — | — | 30 | 3.75 |
| 5 | — | — | — | — | — | — | 60 | 7.5 |
| 6 | — | — | — | — | — | — | 90 | 11.25 |
| 7 | 1 | 125 | — | — | 30 | 3.75 | — | — |
| 8 | 2 | 250 | — | — | 30 | 3.75 | — | — |
| 9 | 1 | 125 | — | — | 60 | 7.5 | — | — |
| 10 | 2 | 250 | — | — | 60 | 7.5 | — | — |
| 11 | 1 | 125 | — | — | 90 | 11.55 | — | — |
| 12 | 2 | 250 | — | — | 90 | 11.25 | — | — |
| 13 | 1 | 125 | — | — | — | — | 30 | 3.75 |
| 14 | 1 | 125 | — | — | — | — | 60 | 7.5 |
| 15 | 2 | 250 | — | — | — | — | 30 | 3.75 |
| 16 | 2 | 250 | — | — | — | — | 60 | 7.5 |
| 17 | 1 | 125 | — | — | — | — | 90 | 11.25 |
| 18 | 2 | 250 | — | — | — | — | 90 | 11.25 |
| 19 | — | — | 25 | 3.125 | 30 | 3.75 | — | — |
| 20 | — | — | 50 | 6.25 | 30 | 3.75 | — | — |
| 21 | — | — | 25 | 3.125 | 60 | 7.5 | — | — |
| 22 | — | — | 50 | 6.25 | 60 | 7.5 | — | — |
| 23 | — | — | 25 | 3.125 | 90 | 11.25 | — | — |
| 24 | — | — | 50 | 6.25 | 90 | 11.25 | — | — |
| 25 | — | — | 25 | 3.125 | — | — | 30 | 3.75 |
| 26 | — | — | 50 | 6.25 | — | — | 30 | 3.75 |
| 27 | — | — | 25 | 3.125 | — | — | 60 | 7.5 |
| 28 | — | — | 50 | 6.25 | — | — | 60 | 7.5 |
| 29 | — | — | 25 | 3.125 | — | — | 90 | 11.25 |
| 30 | — | — | 50 | 6.25 | — | — | 90 | 11.25 |
| 31 | 1 | 125 | 25 | 3.125 | 30 | 3.75 | — | — |
| 32 | 1 | 125 | 50 | 6.25 | 30 | 3.75 | — | — |
| 33 | 1 | 125 | 25 | 3.125 | 60 | 7.5 | — | — |
| 34 | 1 | 125 | 50 | 6.25 | 60 | 7.5 | — | — |
| 35 | 1 | 125 | 25 | 3.125 | 90 | 11.25 | — | — |
| 36 | 1 | 125 | 50 | 6.25 | 90 | 11.25 | — | — |
| 37 | 1 | 125 | 25 | 3.125 | — | — | 30 | 3.75 |
| 38 | 1 | 125 | 50 | 6.25 | — | — | 30 | 3.75 |
| 39 | 1 | 125 | 25 | 3.125 | — | — | 60 | 7.5 |
| 40 | 1 | 125 | 50 | 6.25 | — | — | 60 | 7.5 |
| 41 | 1 | 125 | 25 | 3.125 | — | — | 90 | 11.25 |
| 42 | 1 | 125 | 50 | 6.25 | — | — | 90 | 11.25 |
| 43 | 2 | 250 | 25 | 3.125 | 30 | 3.75 | — | — |
| 44 | 2 | 250 | 50 | 6.25 | 30 | 3.75 | — | — |
| 45 | 2 | 250 | 25 | 3.125 | 60 | 7.5 | — | — |
| 46 | 2 | 250 | 50 | 6.25 | 60 | 7.5 | — | — |
| 47 | 2 | 250 | 25 | 3.125 | 90 | 11.25 | — | — |
| 48 | 2 | 250 | 50 | 6.25 | 90 | 11.25 | — | — |
| 49 | 2 | 250 | 25 | 3.125 | — | — | 30 | 3.75 |
| 50 | 2 | 250 | 50 | 6.25 | — | — | 30 | 3.75 |
| 51 | 2 | 250 | 25 | 3.125 | — | — | 60 | 7.5 |
| 52 | 2 | 250 | 50 | 6.25 | — | — | 60 | 7.5 |
| 53 | 2 | 250 | 25 | 3.125 | — | — | 90 | 11.25 |
| 54 | 2 | 250 | 50 | 6.25 | — | — | 90 | 11.25 |

Figure 6:
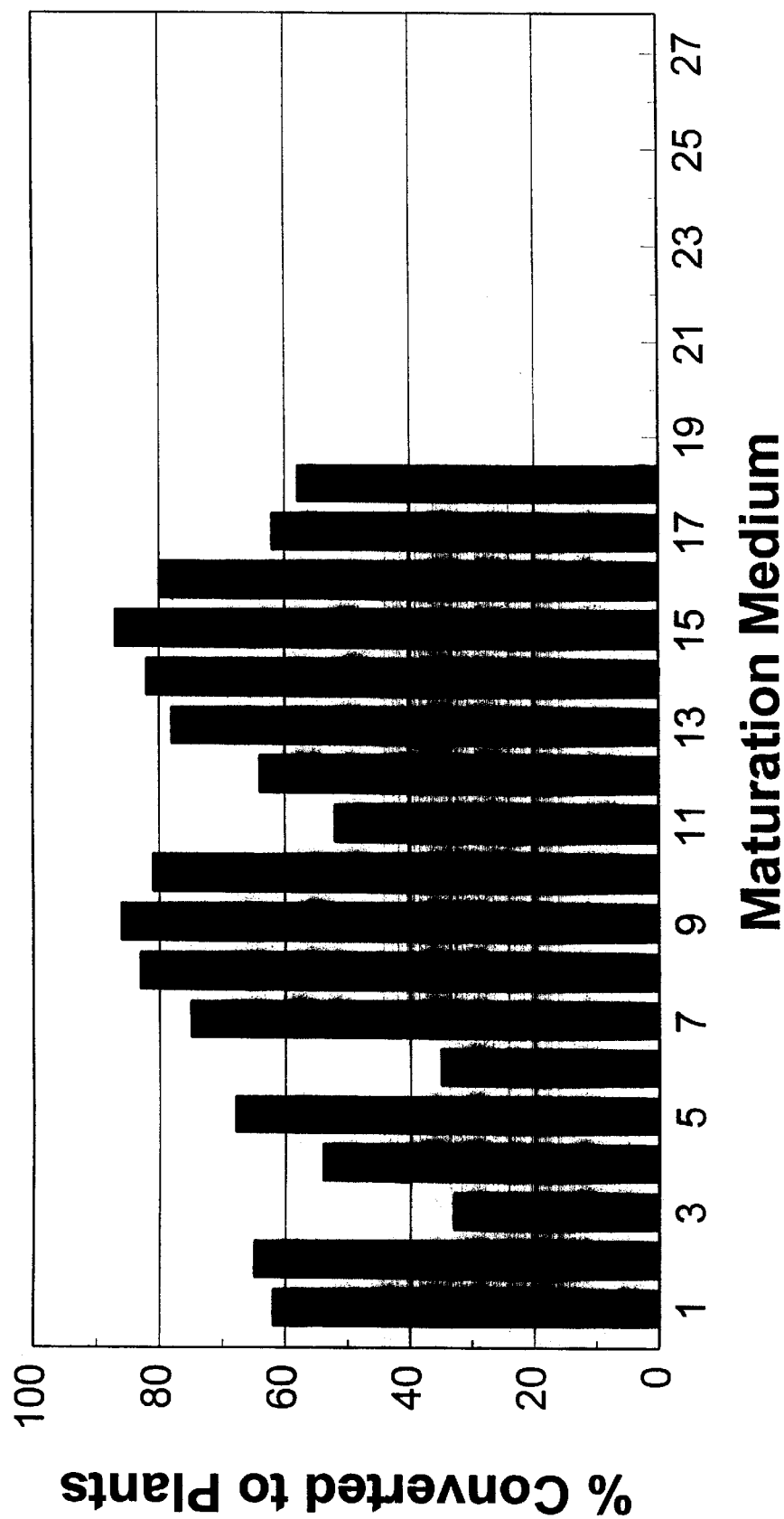
FIGS. 6 and 7 are graphical illustrations of the conversion rate of embryos to plants by maturing the embryos on various media.
Figure 7:
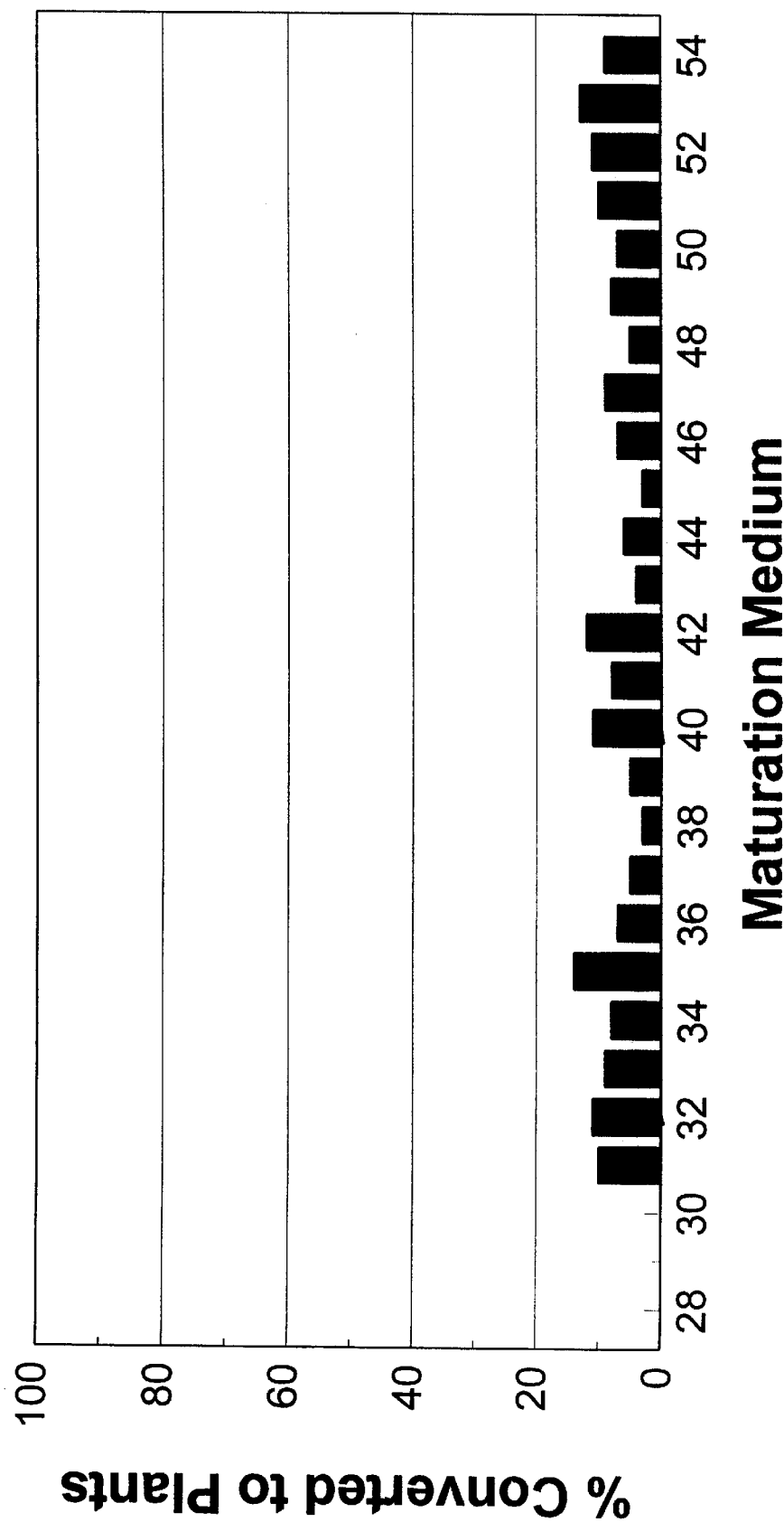

Of the foregoing samples, media containing maltose and/or sucrose alone or in combination with ABA were found to be useful for maturation treatment. Accordingly, samples 1–18 were found to be the most suitable media for maturation treatment and were successful in terms of conversion from mature embryos into plants. The results of the use of various maturation media as described in Table 2 are illustrated graphically in FIGS. 6 and 7. The percentage conversion of embryos to plants is greatest on maturation media containing maltose or sucrose alone or either one in combination with abscisic acid.

Having described the invention and preferred embodiments thereof, it will be recognized that various modifications, substitutions and rearrangements may be made by those of ordinary skill without departing from the spirit and scope of the appended claims.

What is claimed is:

1. A method for producing embryos for propagation of sweetgum which comprises:

collecting male inflorescence tissue from a mature sweetgum tree;

disinfesting the inflorescence tissue;

culturing the disinfested tissue on a plant cell growth medium comprising a basal medium containing from about 0.01 to about 5 milligrams per liter of N-phenyl-N-1,2,3-thiadaizol-5-ylurea (TDZ) and from about 0.01 to about 3 milligrams per liter 2,4-dichlorophenoxyacetic acid (2,4-D) to produce somatic embryos; and maturing the somatic embryos in a maturation medium containing a precocious germination inhibitor and, optionally, one or more sugars.

2. The method of claim 1 wherein the step of disinfesting comprises washing the tissue under sterile conditions with about 70% (vol./vol.) ethanol for about 30 seconds to about 5 minutes, about 30% (vol./vol.) antimicrobial wash solution for about 2 to about 15 minutes, about 10 to about 30% (vol./vol.) sodium hypochlorite solution containing about 5% (vol./vol.) sodium hypochlorite for about 2 to about 15 minutes, about 3% (vol./vol.) hydrogen peroxide for about 5 to about 15 minutes and sterile water for about 2 to about 30 minutes.

3. The method of claim 1 wherein the male inflorescence tissue comprises stamens.

4. The method of claim 1 wherein the male inflorescence tissue comprises axes.

5. The method of claim 1 further comprising collecting proembryogenic masses from the plant cell growth medium and culturing the PEMs in a second plant growth medium to increase the masses of the PEMs.

6. The method of claim 5 further comprising fractionating the cultured masses through a stainless steel mesh having apertures of from about 100 to about 400 microns.

7. The method of claim 6 further comprising filtering and treating the fractionated PEMs on a growth medium containing activated charcoal and substantially no growth regulators to remove the TDZ and 2,4-D therefrom and cause formation of somatic embryos from the PEMs.

8. The method of claim 1 wherein the precocious germination inhibitor comprises abscisic acid.

9. The method of claim 8 wherein the one or more sugars in the maturation medium comprise sucrose and maltose.

10. The method of claim 8 wherein the one or more sugars in the maturation medium comprise sucrose.

11. The method of claim 8 wherein the one or more sugars in the maturation medium comprise maltose.

12. The method of claim 8 further comprising collecting mature somatic embryos from the maturation medium and desiccating the embryos to a moisture content within the range of from about 8 to about 75 percent by weight.

13. The method of claim 12 further comprising treating the desiccated embryos by cold stratification.

14. A method for propagating sweetgum from plant tissue which comprises:

collecting male inflorescence tissue from a mature sweetgum tree;

disinfesting the inflorescence tissue by treating the tissue with about 70% (vol./vol.) ethanol for about 30 seconds to 5 about minutes, about 30% (vol./vol.) antimicrobial wash solution for about 2 to about 15 minutes, about 10 to about 30% (vol./vol.) sodium hypochlorite solution containing about 5% (vol./vol.) sodium hypochlorite for about 2 to about 15 minutes, about 3% (vol./vol.) hydrogen peroxide for about 5 to about 15 minutes and sterile water for about 2 to about 30 minutes; and culturing the disinfected tissue on a plant cell growth medium containing about 0.01 to about 2.5 milligrams per liter of N-phenyl-N-1,2,3-thiadiazol-5-ylurea (TDZ) to produce somatic embryos and proembryogenic masses (PEMs).

15. The method of claim 14 wherein the male inflorescence tissue comprises stamens.

16. The method of claim 14 wherein the male inflorescence tissue comprises axes.

17. The method of claim 14 further comprising collecting PEMs from the plant cell growth medium and culturing the PEMs in a second plant growth medium.

18. The method of claim 17 further comprising fractionating the cultured PEMs through a stainless steel mesh having apertures of from about 100 to about 400 microns.

19. The method of claim 18 further comprising filtering and treating the fractionated PEMs on a growth medium containing activated charcoal and substantially no growth regulators to remove TDZ therefrom and cause formation somatic embryos from the PEMs.

20. The method of claim 19 further comprising plating the filtered and treated PEMs onto a medium containing abscisic acid.

21. The method of claim 20 wherein the medium further comprises sucrose and maltose.

22. The method of claim 20 wherein the medium further comprises sucrose.

23. The method of claim 20 wherein the medium further comprises maltose.

24. The method of claim 21 further comprising collecting mature somatic embryos from the medium and desiccating the embryos to a moisture content within the range of from about 8 to about 75 percent by weight.

25. The method of claim 24 further comprising treating the desiccated embryos by cold stratification.

26. A method for propagating sweetgum from explant tissue which comprises:

disinfesting male inflorescence tissue from a mature sweetgum tree;

culturing the tissue on a first growth medium which induces production of cells from the tissue which cells exhibit unequal cell division;

transferring cells which exhibit unequal cell division from the first growth medium to a second growth medium for inducing the growth of proembryogenic masses (PEMs);

collecting PEMs from the second growth medium and culturing the PEMs in a third growth medium to further promote the growth of the PEMs;

size fractionating PEMs from the third growth medium through a mesh having apertures ranging from about 100 to about 400 microns;

plating the fractioned PEMs onto a growth medium containing activated charcoal and substantially no growth regulators to produce somatic embryos;

plating the somatic embryos from the fractionated PEMs onto a maturation growth medium and subjecting the somatic embryos thereon to a maturation treatment to produce mature somatic embryos;

collecting mature somatic embryos from the maturation growth medium and desiccating the mature somatic embryos to a moisture content of from about 8 to about 75 percent by weight; and treating the desiccated embryos by cold stratification.

27. The method of claim 26 wherein the maturation growth medium comprises abscisic acid.

28. The method of claim 27 wherein the maturation growth medium further comprises sucrose and maltose.

29. The method of claim 26 wherein the first and second mediums contains from about 0.01 to about 2.5 milligrams per liter of N-phenyl-N-1,2,3-thiadiazol-5-ylurea.

30. The method of claim 26 wherein the tissue is disinfested by treating the tissue with about 70% (vol./vol.) ethanol for about 30 seconds to about 5 minutes, about 30% (vol./vol.) antimicrobial wash solution for about 2 to about 15 minutes, about 10 to about 30% (vol./vol.) sodium hypochlorite solution containing about 5% (vol./vol.) sodium hypochlorite for about 2 to about 15 minutes, about 3% (vol./vol.) hydrogen peroxide for about 5 to about 15 minutes and sterile water for about 2 to about 30 minutes.

* * * * *

UNITED STATES PATENT AND TRADEMARK OFFICE
CERTIFICATE OF CORRECTION

PATENT NO. : 5,840,581          Page 1 of 2
DATED      : November 24, 1998
INVENTOR(S) : Daniel T. Carraway and Scott A. Merkle It is certified that error appears in the above-identified patent and that said Letters Patent is hereby corrected as shown below:

Column 4, line 57, after "preferably", delete "in"

<u>In the Claims</u>:

Claim 5, Column 9, line 29, after "masses", add "(PEMs)"

Claim 6, Column 9, line 34, after "cultured", delete "masses" and insert therefor --PEMs--.

Claim 14, Column 9, line 61, after "to", delete "5 about" and insert therefor --about 5--.

Claim 20, Column 10, line 22, after "onto a" and before "medium", insert "maturation".

Claim 21, Column 10, line 24, after "wherein the" and before "medium", insert --maturation--.

UNITED STATES PATENT AND TRADEMARK OFFICE
CERTIFICATE OF CORRECTION

PATENT NO.   : 5,840,581
DATED        : November 24, 1998
INVENTOR(S)  : Daniel T. Carraway and Scott A. Merkle It is certified that error appears in the above-identified patent and that said Letters Patent is hereby corrected as shown below:

Claim 22, Column 10, line 26, after "wherein the" and before "medium", insert --maturation--.

Claim 23, Column 10, line 28, after "wherein the" and before "medium", insert --maturation--.

Claim 24, Column 10, line 31 after "from the" and before "medium", insert --maturation--.

Signed and Sealed this

Thirteenth Day of July, 1999

Attest:

Attesting Officer

Q. TODD DICKINSON

Acting Commissioner of Patents and Trademarks